United States Patent
Cao et al.

(10) Patent No.: US 9,439,638 B2
(45) Date of Patent: Sep. 13, 2016

(54) EXPOSURE APPARATUS FOR PARASPINAL MUSCLE CLEARANCE APPROACH WITH POSTERIORSPINAL SMALL INCISION

(71) Applicant: THE FIRST AFFILIATED HOSPITAL OF NANJING MEDICAL UNIVERSITY, Nanjing, Jiangsu (CN)

(72) Inventors: Xiaojian Cao, Jiangsu (CN); Haijun Li, Jiangsu (CN); Jian Tang, Jiangsu (CN); Hao Xie, Jiangsu (CN)

(73) Assignee: THE FIRST AFFILIATED HOSPITAL OF NANJING MEDICAL UNIVERSITY (CN)

( * ) Notice: Subject to any disclaimer, the term of this patent is extended or adjusted under 35 U.S.C. 154(b) by 0 days.

(21) Appl. No.: 14/764,473

(22) PCT Filed: Nov. 12, 2013

(86) PCT No.: PCT/CN2013/086967
§ 371 (c)(1),
(2) Date: Jul. 29, 2015

(87) PCT Pub. No.: WO2014/117561
PCT Pub. Date: Aug. 7, 2014

(65) Prior Publication Data
US 2015/0359527 A1   Dec. 17, 2015

(30) Foreign Application Priority Data

Jan. 30, 2013   (CN) .......................... 2013 1 0035412

(51) Int. Cl.
*A61B 1/32*   (2006.01)
*A61B 17/02*   (2006.01)
*A61B 17/00*   (2006.01)

(52) U.S. Cl.
CPC ........... *A61B 17/02* (2013.01); *A61B 17/0218* (2013.01); *A61B 2017/0042* (2013.01); *A61B 2017/00858* (2013.01)

(58) Field of Classification Search
CPC .................... A61B 17/025; A61B 2017/0256
USPC ................ 600/201, 204, 210, 217, 219, 226
See application file for complete search history.

(56) References Cited

U.S. PATENT DOCUMENTS 4,817,587 A * 4/1989 Janese ................ A61B 17/0293
                                                           600/210
5,431,153 A   7/1995 Lee
(Continued)

FOREIGN PATENT DOCUMENTS

CN        2138968 Y    7/1993
CN      102166125 A    8/2011
(Continued)

OTHER PUBLICATIONS

International Search Report; PCT/CN2013/086967; International Filing Date: Nov. 12, 2013; 3 Pgs.

*Primary Examiner* — Ellen C Hammond
*Assistant Examiner* — Christina Negrellirodrigue
(74) *Attorney, Agent, or Firm* — Schmeiser, Olsen & Watts, LLP

(57) ABSTRACT

An exposure apparatus for a paraspinal muscle clearance approach with a posterior spinal small incision includes a spinous process side vertebral plate retractor and a cooperating vertebral arch outer side retractor is provided. The apparatus can be used to separate a clearance between a multifidus muscle and a longissimus muscle under direct view, easily and atraumatically reach a screw fixation position on a vertebral arch pedicle, expose a facet joint, bluntly separate the multifidus muscle from the vertebral arch, accurately place the retractors, and thereafter locally form a surgical operation tunnel space that externally extends 10 degrees to 15 degrees. A design of angles and structures of retractors effectively protects local soft tissues and prevents a tissue damage while executing traction on local muscles and ensuring an adequate surgical space.

2 Claims, 1 Drawing Sheet

(56) References Cited

U.S. PATENT DOCUMENTS

Figure 1:
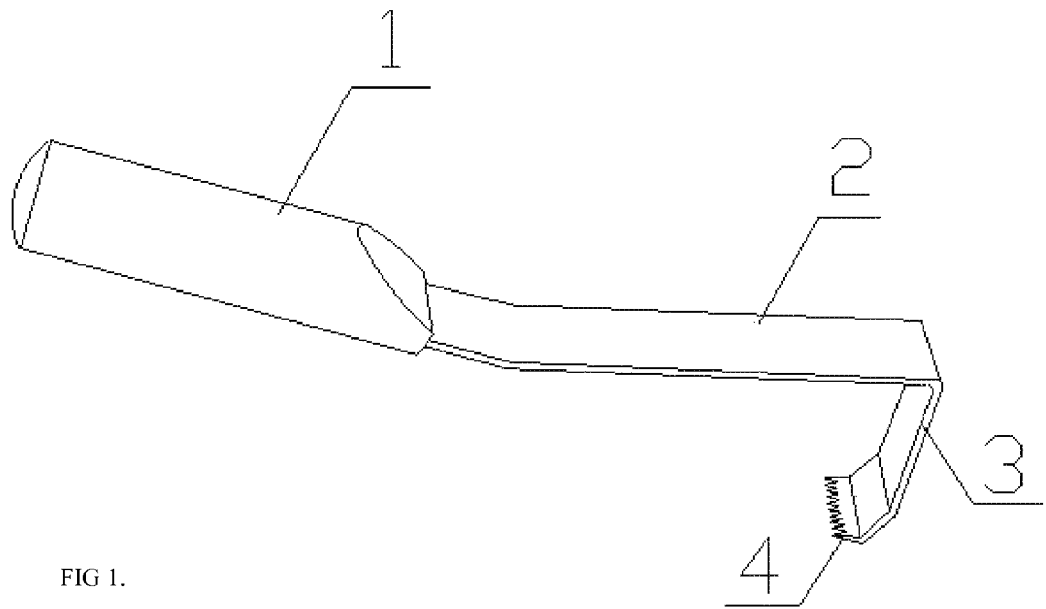

| | | | |
|---|---|---|---|
| 6,951,538 B2 * | 10/2005 | Ritland | A61B 17/1757 600/210 |
| 7,455,639 B2 * | 11/2008 | Ritland | A61B 17/02 600/201 |
| 2002/0013514 A1 | 1/2002 | Brau | |
| 2005/0228233 A1 | 10/2005 | Ritland | |

FOREIGN PATENT DOCUMENTS

| | | |
|---|---|---|
| CN | 202051745 U | 11/2011 |
| CN | 103110437 A | 5/2013 |
| CN | 103126731 A | 6/2013 |
| CN | 203059799 U | 7/2013 |
| CN | 203059800 U | 7/2013 |

* cited by examiner

EXPOSURE APPARATUS FOR PARASPINAL MUSCLE CLEARANCE APPROACH WITH POSTERIORSPINAL SMALL INCISION

CROSS-REFERENCE TO RELATED APPLICATIONS

This application claims priority to PCT Application No. PCT/CN2013/086967, having a filing date of Nov. 12, 2013, based off of Chinese Application No. 201310035412.4, having a filing date of Jan. 30, 2013, the entire contents of which are hereby incorporated by reference.

FIELD OF TECHNOLOGY

The following relates to an exposure apparatus for paraspinal muscle clearance approach with posterior spinal small incision, and belongs to the field of medical appliances.

BACKGROUND

Pedicle screw technology has been developed quickly since its introduction in 1980s and has been widely applied to surgical treatment on affections such as spinal degeneration, spondylolisthesis, spinal stenosis, vertebral fracture, malformation, metastatic tumor of bone, spinal unsteadiness and the like. At present, the pedicle screw is one of the internal fixation instruments that are most widely used in a spine surgery, and methods for embedding the pedicle screw mainly include: 1. a posterior mediseciton screw placement surgery, which is a conventional surgery manner, is widely applied in clinic presently, and widely accepted by majority clinicists, but it has the major defects of larger surgery wound, difficult exposure of a needle inlet point at the pedicle, much bleed, longer postoperative recovery time for the patients, multiple combination of atrophy of longissimus muscle and multifidus muscle, instability due to ligament damage, and long-dated lumbago left on partial sufferers. 2. minimally invasive spine technology, i.e., posterior channel aided minimally invasive screw placement technology, which conducts the operation of placing a spinal pedicle screw with the help of such special surgery appliances and instruments like medical images, aided channel expansion and microscopic endoscope or the like, achieves the optimal therapeutic effect with minimal injury, and has the advantages of short surgical incision, small wound, less bleeding, rapid postoperative function recovery, and reduction of incidence of postoperative pains on the waist and back when compared with the conventional method. But presently, it has not been widely applied and popularized for being applied in clinic for almost 30 years since it is invented due to the expensive supporting instruments and relatively flat learning curves, and particularly, it is only limited to be developed at the spine surgery of tertiary hospitals at home presently.

A new minimally invasive technology which has the advantages of short surgical incision, small wound, less bleeding, rapid postoperative function recovery that are similar to a minimally invasive surgery, is simple and effective, and is easy to grasp, is needed in clinic presently. The inventor redesigns a set of surgical manner and surgical instrument, and improves the posterior spinal minimally invasive technology, which are simple and convenient, easier to grasp, have smaller wound than that of the conventional minimally invasive surgery, while the exposure apparatus for paraspinal muscle clearance approach with posterior spinal small incision is just a part thereof.

The conventional posterior spinal minimally invasive vertebral plate depression technology generally employs a kirschner wire to puncture and position the vertebral plate and then incise the skin, use an expander to expand from small to big in sequence till obtaining a satisfied size, wherein the puncture approach may deviate the clearance between the multifidus muscle and the longissimus muscle and enter the multifidus muscle or the longissimus muscle to cause injury of the multifidus muscle and the longissimus muscle, and meanwhile, the expansion process thereof is to tear and draw partial muscles actually, which further aggravates the muscular injury.

SUMMARY

An aspect relates to providing an exposure apparatus which can aid to accurately, quickly and conveniently separate a clearance between a multifidus muscle and a longissimus muscle under direct vision during a posterior minimally invasive vertebral plate depression operation, and can easily and atraumatically reach a vertebral plate depression position.

Another aspect relates to an exposure apparatus for paraspinal muscle clearance approach with posterior spinal small incision includes a spinous process side vertebral plate retractor and a cooperating vertebral arch outer side retractor, wherein the spinous process side vertebral plate retractor consists of a first handle and a first retractor body, the first retractor body is an L-shaped metal bar, one end of the first retractor body is fixedly connected to the first handle, the other end of the first retractor bends towards the direction of the first handle, the end is provided with a horizontal gear part along the width direction of the first retractor body, the horizontal gear part is located at one side of the other end of the first retractor body close to the first handle, and an included angle formed between the horizontal gear part and the end is an obtuse angle; the vertebral plate outer side retractor consists of a second handle and a second retractor body, the second retractor body is an L-shaped metal bar, one end of the second retractor body is connected to the second handle, and the other end of the second retractor body is provided with a linguiform bulge that bends towards a direction far away from the second handle.

As a further improvement of the foregoing technical solution, the first retractor body includes a first horizontal segment and a first vertical segment, wherein an included angle of 80±10 degrees is formed between the first horizontal segment and the first vertical segment so as to satisfy the requirement that the surgical approach needs to externally extend for a certain angle; a folded angle of 165±15 degrees is formed between the first handle and the first horizontal segment, the first handle is located at one side of the first horizontal segment opposite to the first vertical segment so as to be convenient for holding during traction in the surgery, and reduce the influences of tissues surrounding the incision on placing the retractor; and the other end of the first retractor body bends by 10±10 degrees towards the direction of the first handle.

As a further improvement of the foregoing technical solution, the second retractor body includes a second horizontal segment and a second vertical segment, wherein an included angle of 100±10 degrees is formed between the second horizontal segment and the second vertical segment so as to satisfy the requirement that the surgical approach needs to externally extend for a certain angle while exposing the vertebral plate; a folded angle of 165±15 degrees is formed between the second handle and the second horizontal segment, and the second handle is located at one side of the second horizontal segment opposite to the second vertical segment so as to be convenient for holding during traction in the surgery, and reduce the influences of tissues surrounding the incision on placing the retractor; and the other end of the second retractor body bends by 10±5 degrees towards a direction far away from the second handle.

Further, both the connecting ends of the first handle and the second handle are a fishmouth shaped flat structure, which avoid the oppression of the retractor on the tissues during the surgery, and are beneficial for operating the surgery; both the thicknesses of the first retractor body and the second retractor body are 2±1 mm, and the widths thereof are both 25±5 mm; and both the lengths of the first horizontal segment and the second horizontal segment are 100±50 mm.

Further, the length of the first vertical segment is 40±10 or 60±10 mm, the length of the other end of the first retractor body bending towards the direction of the first handle is 10±5 mm, and the length of the gear of the horizontal gear part is 5±2 mm, which can effectively pull the multifidus muscle towards the inside and then lift the multifidus muscle upwards, completely expose the vertebral plate, is beneficial for the surgical operation, and has smaller injury on local muscle. Further, the length of the second vertical segment is 55±10 or 75±10 mm, and the other end of the second retractor body is provided with two linguiform bulges having a length of 5±2 mm, wherein the linguiform bulges are pushed against the outer rim of the vertebral plate, which can locally expose the vertebral plate, and meanwhile the two linguiform bulges make the contact between the retractor and the vertebral plate more stable, and implement easy and labor-saving local exposure operation.

Further, the outer surfaces of the holding portions of the first handle and the second handle are engraved with crossed pinstripes so as to be convenient for holding during the surgery.

Compared with the prior art, embodiments of the present invention have the advantageous effects that: (1) the two roughed handles are convenient for the surgeon to hold, and the fishmouth shaped design of the connecting ends of the handle avoids the oppression injury of the retractor on the tissues during the surgery; and the folded angle employed between the handle and the retractor enables the holding portion of the handle upwarped, thus reducing the influences of tissues surrounding the incision on the retractor; (2) the two retractors are convenient to separate the clearance between the multifidus muscle and the longissimus muscle under direct view at the paraspinal muscle approach with posterior spinal small incision, expose the vertebral plate, avoid muscle injury caused by entering the inside of a muscle group, and reduce bleeding during the surgery; (3) the unique gear-bulge structure design of the vertebral plate side retractor enables the retractor to pull the multifidus muscle towards the inside and also lift upwards at the same time during the surgery, thus not only playing the role of pulling the multifidus muscle to expose the vertebral plate, but also being capable of avoiding the multifidus muscle from being pressed between the spinous process and the retractor and protecting the multifidus muscle from injury; (4) the two linguiform bulges are employed on the position contacted with the outer rim of the vertebral plate, and pushed against the outer rim of the vertebral plate during the surgery so as to be capable of locally exposing the vertebral plate; meanwhile, the two linguiform bulges make the contact between the retractor and the vertebral plate more stable, and implement simple and labor-saving local exposure operation; and (5) embodiments of the present invention are designed according to a characteristic of local surgical approach muscles and a characteristic of local bone structures; after finishing the dissection of the surgical approach and accurately placing the retractor, the design of 80±10 degrees of the spinous process side retractor and the design of 100±10 degrees of the vertebral plate outer side retractor can locally form a tunnel space that externally extends 10 to 15 degrees, which complies with the requirements of local surgical operation.

BRIEF DESCRIPTION

Figure 2:
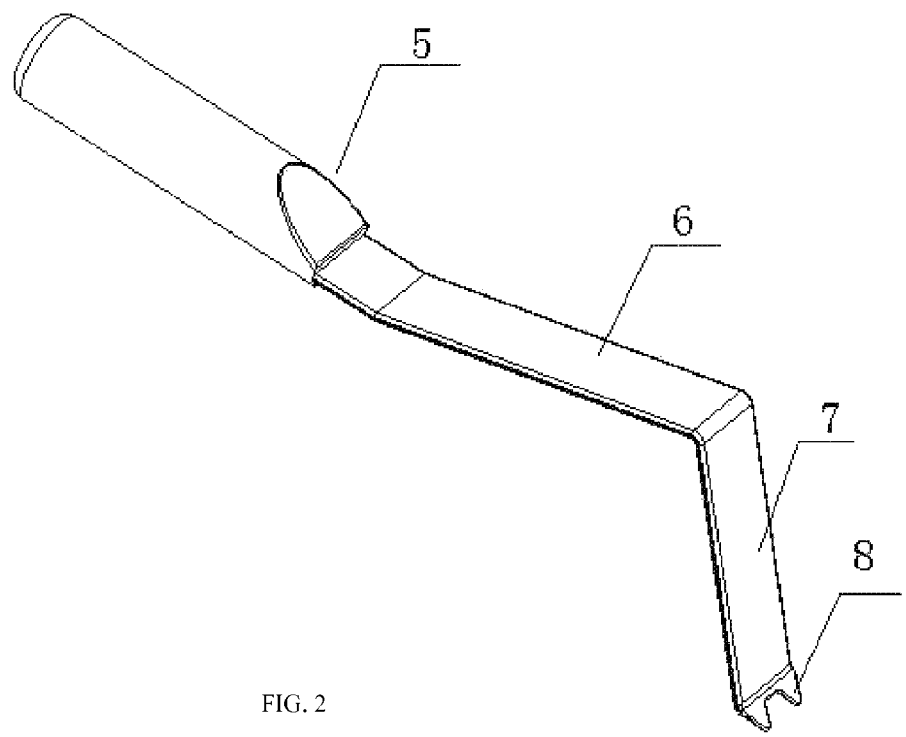

Some of the embodiments will be described in detail, with reference to the following figures, wherein like designations denote like members, wherein:

FIG. 1 is a block diagram of an embodiment of a spinous process side vertebral plate retractor; and FIG. 2 is a block diagram of an embodiment of a vertebral plate outer side retractor.

DETAILED DESCRIPTION

The technical solution of embodiments of the present invention will be described in detail hereinafter, but the protection scope of the present invention is not limited to the embodiment.

First embodiment: as shown in FIG. 1 and FIG. 2, an exposure apparatus for paraspinal muscle clearance approach with posterior spinal small incision includes a spinous process side vertebral plate retractor and a cooperating vertebral arch outer side retractor.

The spinous process side vertebral plate retractor consists of a first handle 1 and a first retractor body, wherein the first retractor body is an L-shaped metal bar, which includes a first horizontal segment 2 and a first vertical segment 3, an included angle between the first horizontal segment 2 and the first vertical segment 3 is 80 degrees, one end of the first retractor is connected to the first handle 1, a folded angle of 165 degrees is formed between the first handle 1 and the first horizontal segment 2, the first handle 1 is located at one side of the first horizontal segment 2 opposite to the first vertical segment 3, the other end of the first retractor body bends towards the direction of the first handle 1 with a bending length of 10 mm and a bending angle of 10 degrees; the end is provided with a horizontal gear part 4 along the width direction of the first retractor body, the horizontal gear part 4 is located at one side of the other end of the first retractor body close to the first handle 1, and an included angle formed between the horizontal gear part and the end is an obtuse angle; the horizontal gear part is parallel to the first horizontal segment 2, and the length of the gear of the horizontal gear part 4 is 5 mm.

The vertebral plate outer side retractor consists of a second handle 5 and a second retractor body, wherein the second retractor body is an L-shaped metal bar, the second retractor body includes a second horizontal segment 6 and a second vertical segment 7, an included angle between the second horizontal segment 6 and the second vertical segment 7 is 100 degrees, one end of the second retractor body is connected to the second handle 5, a folded angle of 165 degrees is formed between the second handle 5 and the second horizontal segment 6, the second handle 5 is located at one side of the second horizontal segment 6 opposite to the second vertical segment 7, the other end of the second retractor body is provided with a pair of linguiform bulges 8 bending towards a direction far away from the second handle 5 with a length of 5 mm, wherein the linguiform bulges bend toward the direction far away from the second handle 5 by 10 degrees.

Both the connecting ends of the first handle 1 and the second handle 5 are fishmouth shaped flat structures, both the lengths of the first handle 1 and the second handle 5 are 120 mm, wherein the length of the holding portion is 100 mm, both the first handle and the second handle are circular columns having a diameter of 20 mm, and the outer surfaces of the holding portions are engraved with crossed pinstripes; both the thicknesses of the first retractor body 1 and the second retractor body are 2 mm, and the widths thereof are both 25 mm; both the lengths of the first horizontal segment 2 and the second horizontal segment 6 are 100 mm, the length of the first vertical segment 3 is 400 r 60 mm, and the length of the second vertical segment 7 is 550 r 75 mm.

As described above, although the present invention has been represented and described with reference to the specifically preferred embodiments, it cannot be interpreted as a limit to the present invention itself. Various modifications may be figured out in forms and details without departing from the spirit and range of the present invention defined in the accompanied claims.

The invention claimed is:

1. An exposure apparatus for paraspinal muscle clearance approach with posterior spinal small incision, comprising:
a spinous process side vertebral plate retractor and a cooperating vertebral arch outer side retractor, wherein the spinous process side vertebral plate retractor consists of a first handle and a first retractor body, the first retractor body is an L-shaped metal bar, one end of the first retractor body is fixedly connected to the first handle, the other end of the first retractor body bends towards a direction of the first handle, the end is provided with a horizontal gear part along a width direction of the first retractor body, the horizontal gear part being located at one side of the other end of the first retractor body close to the first handle, and an included angle formed between the horizontal gear part and the end is an obtuse angle;
wherein the cooperating vertebral plate outer side retractor consists of a second handle and a second retractor body, the second retractor body is an L-shaped metal bar, one end of the second retractor body is connected to the second handle, and the other end of the second retractor body is provided with a linguiform bulge that bends towards a direction far away from the second handle;
wherein the first retractor body comprises a first horizontal segment and a first vertical segment, wherein an included angle of 80±10 degrees is formed between the first horizontal segment and the first vertical segment, a folded angle of 165±15 degrees is formed between the first handle and the first horizontal segment, the first handle is located at one side of the first horizontal segment opposite to the first vertical segment, and the other end of the first retractor body bends by 10±10 degrees towards the direction of the first handle;
wherein the second retractor body comprises a second horizontal segment and a second vertical segment, wherein an included angle of 100±10 degrees is formed between the second horizontal segment and the second vertical segment, a folded angle of 165±15 degrees is formed between the second handle and the second horizontal segment, the second handle is located at one side of the second horizontal segment opposite to the second vertical segment, and the other end of the second retractor body bends by 10±5 degrees towards a direction far away from the second handle;
wherein both the connecting ends of the first handle and the second handle are a fishmouth shaped flat structure, both the thicknesses of the first retractor body and the second retractor body are 2±1 mm, and the widths thereof are both 25±10 mm; and both the lengths of the first horizontal segment and the second horizontal segment are 100±50 mm;
wherein the length of the first vertical segment is 40±10 or 60±10 mm, the length of the other end of the first retractor body bending towards the direction of the first handle is 10±5 mm, and the length of the gear of the horizontal gear part is 5±2 mm;
wherein the length of the second vertical segment is 55±10 or 75±10 mm, and the other end of the second retractor body is provided with two linguiform bulges having a length of 5±2 mm.

2. The exposure apparatus for paraspinal muscle clearance approach with posterior spinal small incision according to claim 1, wherein an outer surface of a holding portion of each first handle and second handle are provided with crossed pinstripes.

* * * * *